United States Patent

Wright et al.

[11] Patent Number: 5,326,571
[45] Date of Patent: Jul. 5, 1994

[54] DOSAGE FORMS COMPRISING POLYMERS COMPRISING DIFFERENT MOLECULAR WEIGHTS

[75] Inventors: Jeri D. Wright, Dublin; Brian L. Barclay, Sunnyvale; David R. Swanson, Palo Alto, all of Calif.

[73] Assignee: ALZA Corporation, Santa Clara, Calif.

[21] Appl. No.: 941,332

[22] Filed: Sep. 4, 1992

Related U.S. Application Data

[62] Division of Ser. No. 688,807, Apr. 22, 1991, Pat. No. 5,208,037.

[51] Int. Cl.⁵ .............................. A61K 9/24
[52] U.S. Cl. ........................... 424/473; 424/472; 424/468
[58] Field of Search ............... 424/473, 472, 468

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,202 | 9/1978 | Theeuwes | 128/260 |
| 4,327,725 | 5/1982 | Cortese et al. | 128/260 |
| 4,717,566 | 1/1988 | Eckenhoff et al. | 424/438 |
| 4,765,989 | 8/1988 | Wong et al. | 424/473 |
| 4,783,337 | 11/1988 | Wong et al. | 424/468 |
| 4,816,263 | 3/1989 | Ayer et al. | 424/468 |
| 4,837,111 | 6/1989 | Deters et al. | 424/473 |
| 4,859,470 | 8/1989 | Guittard et al. | 424/473 |
| 4,863,456 | 9/1989 | Stephens et al. | 604/892 |
| 4,902,514 | 2/1990 | Barclay et al. | 424/473 |
| 4,904,474 | 2/1990 | Theeuwes et al. | 424/424 |
| 4,946,687 | 8/1990 | Ayer et al. | 424/473 |
| 4,948,593 | 8/1990 | Wright et al. | 424/473 |
| 4,950,486 | 8/1990 | Ayer et al. | 424/473 |
| 4,966,769 | 10/1990 | Guittard et al. | 424/473 |

*Primary Examiner*—Thurman K. Page
*Assistant Examiner*—Leon R. Horne
*Attorney, Agent, or Firm*—Paul L. Sabatine; Edward L. Mandell; Jean M. Duvall

[57] ABSTRACT

A dosage form is disclosed comprising a wall surrounding a compartment, which comprises a first composition comprising a carboxymethylcellulose and a second composition comprising a higher molecular weight carboxymethylcellulose. The first composition comprises a dosage amount of drug that delivers from the dosage form at a controlled rate over time.

13 Claims, 1 Drawing Sheet

DOSAGE FORMS COMPRISING POLYMERS COMPRISING DIFFERENT MOLECULAR WEIGHTS

CROSS-REFERENCE TO RELATED APPLICATIONS

This application is a division of Ser. No. 07/688,807 filed Apr. 22, 1991 U.S. Pat. No. 5,208,037, which application is incorporated herein by reference and benefit is claimed of its filing date. These applications are assigned to the ALZA Corporation of Palo Alto, Calif.

FIELD OF THE INVENTION

The present invention pertains to a dosage form with improved drug delivery capabilities. More particularly, the dosage form comprises a first composition comprising a drug and a carboxymethylcellulose, and a second composition comprising a carboxymethylcellulose comprising a higher molecular weight then the carboxymethylcellulose in the first composition. The first and second compositions cooperate to deliver a maximum dose of drug with a minimum of residual drug left in the dosage form.

BACKGROUND OF THE INVENTION

Controlled release dosage forms are increasingly important for delivering drugs to an animal for obtaining good therapy. The controlled release of drug by a dosage form indicates control is exercised over both the duration and the profile of a drug release program. Controlled release dosage forms provide many therapeutic advantages over conventional dosage forms. For example, one major and important advantage is the lessening of fluctuation in blood plasma drug concentrations. The pharmacologic basis for minimizing fluctuations in plasma level derives from three therapeutic principles. First, every drug has a therapeutic blood level that must be reached if the desired therapeutic benefit is to be achieved from the administered drug. Second, most drugs have blood plasma levels that define the limits above which side effects may appear, and this can be substantially avoided by the use of controlled release dosage forms. Third, the drug plasma concentration response for most drugs is proportional to the concentration administered, which dictates of the need for controlled release dosage forms. These pharmacologic principles indicate a need for keeping plasma concentrations within a therapeutic level, and accordingly, addresses the need for a controlled release dosage form to achieve the intended results.

The dosage form used for drug administration can influence the course of therapeutic activity by affecting the profile of drug concentration in the blood. For example, the blood level profile of a drug following administration by a prior art conventional dosage form is defined by an initial high peak, followed by a rapid decline, in both the slope and the duration of the drug. The initial high peak typically substantially exceeds the therapeutic plasma concentration range and the level fluctuates in peaks and troughs above and below the desired therapeutic level. In contrast, controlled release dosage forms can minimize the fluctuations known to the prior art, minimize or even avoid the peaks in blood level concentration and the following valley in blood level concentrations. A controlled dosage form can extend also the duration of therapeutic index levels over time.

In view of the above presentation it is immediately evident a pressing need exists for a controlled release dosage form for administering a therapeutically-important drug, such as a calcium channel blocking drug to a patient in need of calcium channel blocking therapy. The expression "calcium channel blocking drugs" also are known as calcium channel blockers, calcium channel antagonist, or calcium antagonists. The calcium channel blockers possess broad pharmacological use and they exhibit pronounced properties such as long-lasting vasodilating effects accompanied by an energy-sparing effect on cardiac metabolism, antiarrhythmic and antianginal action on cardiac muscle, vascular spasmolytic action, antihypertensive action, spasmolytic action on smooth muscle of the gastrointestinal and urogenital tracts and the cerebrovascular and respiratory system, useful for antihypercholesterolemic action, protection of the ischemic myocardium, inhibition of irritable bowel syndrome and esophagal spasm, inhibition of migraine, inhibit vascular calcium contraction, reduce cardiac contractile force, inhibit calcium mediated tracheal contraction, inhibit calcium uptake in primary cells, myocardial ischemia and hypertension. The calcium antagonist drugs that possess these therapeutic properties and can be administered by the dosage form and the method of the invention comprise a member selected from the group consisting of verapamil, nifedipine, diltiazem, bepridil, nicardipine, nitredipine, isradipine, niludepine, nisoldipine, felodipine, cinnarizine, flunarizine, perhexiline, amlodipine, or as their pharmaceutically acceptable salts or as their pharmaceutically acceptable derivatives. The pharmaceutically acceptable salts are acid addition salts of non-toxic pharmaceutically acceptable acids. The acids include inorganic acids and organic acids, and consequently, the salt can be an inorganic or organic salt. The pharmaceutically acceptable salts for the purpose of this invention consist of a member selected from the group consisting of inorganic, hydrochloric, hydrobromic, hydriodic, phosphoric, sulfuric, nitric, and the like, organic, trifluoroacetic, trichloroacetic, acetic, glycolic, pamoic, pyruvic, malonic, succinic, maleic, fumaric, malic, tartaric, citric, mandelic, benzoic, cinnamic, methane sulfonic, ethane sulfonic, salicylic, p-toluenesulfonic or cyclohexanesulfamic. The pharmaceutically acceptable derivatives include alkyl substituted and ester derivatives. The drugs are known to the medical art in *USAN and the USP Dictionary of Drug Names*, 1961–1990 Cumulative List, published 1990 by United States Pharmacopeial Convention, Inc.; and in *Physician's Desk Reference*, 45 Ed. 1991, published by Medical Economy Company, Inc.

BACKGROUND PRIOR ART

Dosage forms manufactured as osmotic devices for delivering a drug to an environment of use are known to the prior art in U.S. Pat. No. 3,845,770 issued to Felix Theeuwes and Takeru Higuchi and in U.S. Pat. No. 3,916,899, issued to the same patentees. The osmotic devices disclosed in those patents comprise a semipermeable wall that surrounds a compartment containing a drug. The wall is permeable to the passage of an external fluid, and substantially impermeable to the passage of drug. There is a passageway through the wall for delivering the drug from the device. These devices release drug by fluid being imbibed through the wall into the compartment at a rate determined by the permeability of the wall and the osmotic pressure gradient across the wall to produce an aqueous solution containing drug that is dispensed through the passageway from the device. These devices are effective for delivering a drug in an aqueous solution but often they do not contemplate delivering substantially all of the drug present in a thixotropic pharmaceutically acceptable carrier.

A pioneer advancement in osmotic delivery devices was presented to the art by inventor Felix Theeuwes in U.S. Pat. No. 4,111,202. In this patent, the delivery kinetics of the device are enhanced, for delivering drugs with degrees of solubility in aqueous fluids that are difficult to deliver, such as very soluble or insoluble in the fluid, by manufacturing the device with a drug compartment and an osmagent compartment separated by a film, which film is movable from a rested or essentially straight position to a curved position. The device delivers drugs by fluid being imbibed through the wall into the osmagent compartment producing a solution that causes the compartment to increase in volume and act as a driving force that is applied against the film. This force urges the film to expand against the drug compartment and correspondingly diminish the volume of this compartment, whereby drug is dispensed through the passageway from the device. While this device operates successfully for its intended use, and while it can deliver numerous difficult to deliver drugs, its use can be limited because of the manufacturing steps needed for fabricating and placing the movable film in the device.

In U.S. Pat. No. 4,327,725 patentees Cortese and Theeuwes provided an osmotic dispensing device for delivering beneficial drugs that, because of their solubilities in aqueous and biological fluids, are difficult to deliver in meaningful amounts at controlled rates over time. The osmotic devices of this patent U.S. Pat. No. 4,327,725 comprise a semipermeable wall surrounding a compartment containing a beneficial drug that is insoluble to very soluble in aqueous and biological fluids. The device also contains an expandable hydrogel. In operation, the hydrogel expands in the presence of external fluid that is imbibed into the device and pushes an aqueous drug solution through the passageway from the device. This device operates successfully for its intended use, and it delivers many difficult to deliver beneficial drugs for their intended purpose. However, it has been observed, its use often can be limited because the hydrogel can lack a present ability to imbibe sufficient fluid for the maximum self-expansion needed for pushing all beneficial drugs from the device.

In U.S. Pat. No. 4,765,989 and in U.S. Pat. No. 4,783,337, both patents issued to patentees Wong, Barclay, Deters and Theeuwes, there is provided a novel delivery device for delivering a drug to a patient in need of therapy. The delivery device in these patents comprise a wall permeable to fluid and impermeable to the passage of fluid. An exit port in the wall connects a drug in the compartment with the exterior of the delivery device. The device comprises a first and second composition comprising a mixture of methylcellulose, agar and carboxymethylcellulose or a mixture of hydroxypropylmethylcellulose and sodium carboxymethylcellulose. The patents do not teach regulating and controlling the thixotropic behavior of the composition for delivering substantially all of the drug and concomitantly the release rate behavior characteristics of the delivery device.

The prior art in U.S. Pat. No. 4,816,263 issued to Ayer, Swanson and Kuczynski; in U.S. Pat. No. 4,837,111 issued to Deters, Wong, Barclay, Theeuwes and Swanson; in U.S. Pat. No. 4,859,470 issued to Guittard, Wong, Theeuwes and Cortese; in U.S. Pat. No. 4,863,456 issued to Stephens and Wong; in U.S. Pat. No. 4,902,514 issued to Barclay, Wong, Wright and Childers; in U.S. Pat. No. 4,946,687 issued to Ayer, Swanson and Kuczynski; in U.S. Pat. No. 4,948,593 issued to Wright, Childers, Barclay, Wong and Atkinson; in U.S. Pat. No. 4,950,486 issued to Ayer, Swanson and Kuczynski; and in U.S. Pat. No. 4,966,769 issued to Guittard, Wong, Theeuwes and Cortese, the patentees disclosed delivery devices comprising a composition comprising a drug and a composition comprising a polymer for pushing the drug from the device, however, these patents do not teach two different molecular weight polymers operating together to avoid residual drugs in the device at the end of the drug delivery period. The prior art devices of the above patents are effective for their intended purpose, but they do not teach a unique difference and an accompanying cooperating relationship between two compositions comprising dissimilar polymers for controlled drug delivery over time.

It will be appreciated by those versed in the drug delivery art, that if a delivery device is provided that comprises different internal compositions that exhibit a high level of hydrodynamic and osmotic activity for delivery a drug at a controlled rate for therapy, such a delivery device would have a positive value and represent an advancement in the delivery art. Likewise, it will be immediately appreciated by those versed in the dispensing art that if a delivery device is made available possessing thermodynamic activity for delivering controlled doses of a drug, such a dispensing device would find a practical application in pharmacy and in medicine. Now, it has been found that delivery devices can be enhanced by using different hydrogel polymers for providing maximum self-delivery of drug and maximum self-expansion of the polymer for urging substantially all of the drug from the device.

OBJECTS OF THE INVENTION

Accordingly, in view of above presentation, it is an immediate object of this invention to provide a dosage form manufactured as a drug delivery device for providing an advancement over the prior art.

Another object of the invention is to provide a dosage form manufactured as a delivery device comprising a first composition and a different second composition for delivering essentially all of a drug to a patient over time.

Another object of the invention is to provide a dosage form comprising a first composition comprising a drug and a selected cellulose polymer and a second composition comprising a different selected cellulosic polymer from the polymer in the first composition for improving the delivery characteristics of the dosage form.

Another object of the invention is to provide a dosage form comprising two separate compositions with each composition comprising a different molecular weight polymer for delivering a drug at a controlled rate over a prolonged period of time from 30 minutes to 24 hours.

Another object of the invention is to provide a dosage form for delivering in vivo a calcium channel blocking drug that can be delivered from the device by using two different polymers for good therapy.

Another object of the invention is to provide a dosage form that embraces an osmotic structure possessing two compositions that operate as an integrated unit, which dosage form comprises a first osmotic composition comprising a drug and an osmopolymer, and a second composition comprising a different osmopolymer, which first and second compositions act in concert for hydrodynamically and osmotically delivering the drug from the osmotic dosage form.

Another object of the invention is to provide an osmotic dosage form having means for high loading of from 10 nanograms to 750 milligrams of a water soluble or a water insoluble calcium channel blocking drug for delivering the drug by the interaction to two compositions comprising different polymers for delivering the drug at a controlled rate and continuously over time to a drug recipient.

Another object of the invention is to provide an osmotic dosage form comprising a first composition comprising an osmopolymer and a second composition comprising a different osmopolymer which osmopolymers generate distinct osmotic activities independent of the other osmopolymer, but both cooperating to deliver the drug from the device.

Another object of the invention is to provide an osmotic dosage form that can administer a complete pharmaceutical dosage regimen for delivering a calcium channel blocking drug at a controlled rate and continuously for a given time period, the use of which requires intervention only for initiation and possible termination of the therapeutic regimen.

Another object of this invention is to provide an osmotic dosage form which can house a calcium channel blocking drug and dispense the drug in small doses per hour average at a controlled rate to the gastrointestinal tract throughout the length of the gastrointestinal tract following oral administration of the dosage form.

Another object of the invention is to provide an osmotic dosage form manufactured with a compartment comprising a first polymer composition and a second different polymer composition in contacting arrangement that simultaneously maintain their original identity and function as an integrated compositional layers for delivering a drug from the dosage form.

Another object of the invention is to provide a dosage form comprising osmopolymers manufactured free-of-irradiation such as gamma rays, thereby eliminating any potentially dangerous source or irradiation from the dosage form and from a patient.

Another object of the invention is to provide a dosage form free of poly(alkylene oxide) for administering a drug to a recipient in need of controlled drug therapy.

Another object of the invention is to provide an osmotic dosage form comprising osmopolymers made free-of-radiation for enhancing the acceptance of the dosage form by a patient and by a physician.

BRIEF DESCRIPTION OF THE DRAWINGS

In the drawing figures, which are not drawn to scale, but are set forth to illustrate various embodiments of the invention, the drawing figures are as follows.

Drawing

Drawing

Drawing

In the drawings and in the specification like parts in related figures are identified by like parts. The terms appearing earlier in the specification and in the description of the drawings, as well as embodiments thereof, are further detailed elsewhere in the disclosure.

DETAILED DESCRIPTION OF THE DRAWING FIGURES

Figure 1:
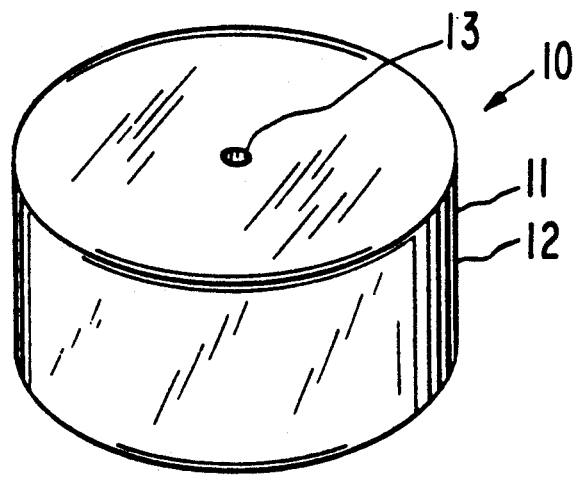
FIG. 1 is a view of an osmotic dosage form sized, shaped and adapted for oral administration into the gastrointestinal tract of a patient in need of drug therapy.
Figure 2:
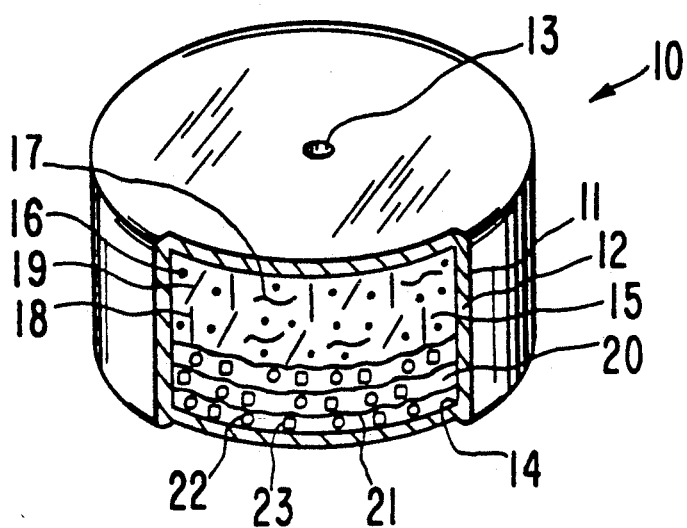
FIG. 2 is an opened view of the osmotic dosage form of drawing FIG. 1 with part of the wall of the dosage form removed for illustrating the structure of the dosage form.

Turning now to the drawing figures in detail, which drawing figures are an example of the dosage form provided by the invention and which example is not to be considered as limiting, one example of an osmotic dosage form is illustrate in drawing FIG. 1 and in drawing FIG. 2.

In drawing FIG. 1, an osmotic dosage form is seen designated by the numeral 10. Dosage form 10 comprises a body member 11 comprising a wall 12 that surrounds and defines an internal compartment, not visible in drawing FIG. 1. Dosage form 10 comprises at least one passageway 13 that connects the interior of dosage form 10 with the exterior biological environment of use.

In drawing FIG. 2, osmotic dosage form 10 is seen in opened view at 14 for illustrating the internal structure of dosage form 10. In drawing FIG. 2, dosage form 10 comprises a body 11 and wall 12. Wall 12 surrounds, forms and defines an internal compartment 15. Wall 12 comprises one passageway 13, or optionally, more than one exit passageway, for dispensing a drug 16 (represented by dots) from compartment 15 of dosage form 10. Drug 16 is defined herein, comprises any drug that can be delivered from dosage form 10 to produce a therapeutic useful result in a patient. In the present application, the term "drug" includes any physiologically or pharmacologically active substance that produces a local or a systemic effect in animals, including warm-blooded mammals, including humans. The drugs that can be delivered by dosage form 10 comprise drugs that are insoluble to highly soluble in aqueous fluids including biological fluids. In one presently preferred embodiment drug 16 comprises a calcium channel blocking drug.

Wall 12 of dosage form 10 comprises a composition that is permeable to the passage of an exterior fluid present in a biological environment of use, and it is substantially impermeable to the passage of drug 16, its salts or its derivatives, and to other ingredients in compartment 15. Wall 12 is substantially inert, nontoxic and it maintains its physical and chemical integrity during the drug dispensing life of dosage form 10. The phrase, "maintains its physical and chemical integrity" means wall 12 does not lose its physical structure during the dispensing life of dosage form 10. Wall 12, in one presently preferred embodiment, comprises a member selected from the group consisting of a cellulose ester, a cellulose ether, or a cellulose ester-ether. In a more presently preferred embodiment, wall 12 comprises a member selected from the group consisting of a cellulose acylate, cellulose diacylate, cellulose triacylate, cellulose acetate, cellulose diacetate, and cellulose triacetate. The cellulose polymeric members comprising wall 12 comprise cellulose acetate having a degree of substitution up to 1 and an acetyl content up to 21%, a cellulose diacetate having a degree of substitution of 1 to 2 and an acetyl content of 21% to 35%, a cellulose triacetate having a degree of substitution of 2 to 3 and an acetyl content of 35% to 44%. The amount of a cellulosic polymer present in wall 12 of dosage form 10 is from 85 weight percent (wt %) to 100 wt %. The cellulosic polymers are known to the art in U.S. Pat. Nos. 3,845,770; 3,816,899; 4,859,470; and 4,863,456; and in Handbook of Common Polymers, by J. R. Scott and W. J. Roff, (1971) published by CRC Press Inc., Cleveland, Ohio. Wall 12 comprises optionally, a flux enhancer, such as a polyethylene glycol that aids in governing fluid flux through semipermeable wall 12. The flux enhancer polyethylene glycol comprises a molecular weight range of 1500 to 7500. The concentration of polyethylene glycol in wall 12, optionally, comprises from 1 wt % to 15 wt %, with the total concentration of the ingredients comprising wall 12 equal to 100 wt %.

Compartment 15, in a drug composition, also identified as a first composition, comprises 20 wt % to 98 wt % of an alkali carboxymethylcellulose ether 17, identified by a wavy line, blended with drug 16. The present invention unexpectedly discovered a carboxymethylcellulose ether 17, or its nontoxic alkali salt, can be used as a thixotropic transport means for drug 16. The amount of drug 16 present in compartment 15 is 2 wt % to 45 wt %. The carboxymethylcellulose ether 17, includes sodium or potassium carboxymethylcellulose, and it possesses an initial gel flow-resistant strength. The carboxymethylcellulose 17 comprising drug 16 on contact by aqueous fluid imbibed into dosage form 10 transforms into a dispensable, thixotropic transport aqueous drug formulation. This dispensable drug formulation, in the presence of a separate osmotic-push force generated in dosage form 10, is subjected to a shear stress applied to the formulation resulting in the formulation being pushed through exit port 13 over 24 hours. The alkali carboxymethylcellulose 17, operable for transporting drug 16 comprises a degree of polymerization of 20 to 1,200, a 10,000 to 300,000 molecular weight and a viscosity of 25 to 1750 cps, centipoises, in a 2% aqueous solution at 25° C. The drug formulation in a preferred manufacture comprises 0 to 40% polyvinylpyrrolidone 18, represented by a vertical line, and comprising a 15,000 to 75,000 molecular weight, from 0 to 40 wt % hydroxypropylcellulose 19, represented by a slant line, comprising a 20,000 to 80,000 molecular weight, and from 0 to 5 wt % of a lubricant such as magnesium stearate, calcium stearate, or stearic acid, with the weight of all ingredients comprising the drug formulation, or the first composition, equal to 100 wt %.

Dosage form 10, in compartment 15, comprises a push formulation 20. Push formulation 20, also identified as a second composition, when dosage form 10 is in operation imbibes a fluid, expands and then pushes the drug composition through exit 13 from dosage form 10. Push composition 20 comprises 65 wt % to 100 wt % of a carboxymethylcellulose 21 comprising a greater than 300,000 to 1,200,000 molecular weight and a degree of polymerization of greater than 1,200 to 4,500. Push composition in a preferred manufacture comprises from 0 wt % to 25 wt % of an osmagent 22, represented by circles, selected from the group consisting of an osmotically active salt, an osmotically active carbohydrate, osmotically active polysaccharide, an osmotically active oxide, or an osmotically active acid solute, from 0 wt % to 25 wt % hydroxypropylmethylcellulose 23, represented by a square, comprising a 9,200 to 20,000 molecular weight, from 0 to 5 wt % lubricant comprising magnesium stearate, stearic acid, or calcium stearate, and 0 to 3 wt % ferric oxide, with the weight of all ingredients in push formulation equal to 100 wt %.

The expression, "exit passageway 13," comprises means and methods suitable for dispensing the beneficial drug 16 from dosage form 10. The exit means includes one passageway, or more than one passageway, that passes through wall 12 for communicating drug 16 in compartment 15 with the exterior of dosage form 10. The expression, "one passageway," includes aperture, orifice, bore, pore, porous element through which drug 16 can be dispensed, a hollow fiber, capillary tube, microporous insert, or microporous overlay. Thus, a wall that is in part microporous is optional with the invention. The expression includes a material that erodes or is leached from wall 12 in the fluid environment of use to produce one passageway, or more than one passageway, of controlled exit releasing dimensions. Representative materials suitable for forming at least one passageway, two passageways, or more, include an erodible poly(glycolic) or poly(lactic) acid member in the wall, a gelatinous filament, poly(vinyl alcohol), leachable materials such as fluid removable pore formers providing exit pores of release rate controlling properties. A passageway or a plurality of passageways can be formed by leaching a material such as sorbitol, mannitol or sodium chloride from the wall. The passageway can have any shape such as round, triangular, square, elliptical, or irregular. The dosage form can be constructed with one or more passageways in a spaced apart relation or a single surface or on more than more distant surfaces of a dosage form. Passageways and equipment for forming passageways are disclosed in U.S. Pat. Nos. 3,916,899; 4,063,064 and 4,088,864. Representative passageways formed by governed leaching of a fluid leachable composition to produce a pore of controlled release rate size are disclosed in U.S. Pat. No. 4,200,098.

Dosage form 10 is manufactured by standard techniques. For example, in one manufacture a drug and the other ingredients comprising the drug formulation are homogeneously blended and pressed into a solid formulation. The pressed formulation possesses dimensions that correspond to the internal dimension of the area occupied by the drug formulation in the dosage form 10. The drug formulation also possesses dimensions corresponding to the dimensions of the push formulation for forming a contacting surface arrangement therewith. In this manufacture, the drug and the other ingredients comprising the compositions are blended with a solvent and mixed into a solid or semisolid form by conventional methods such as ballmilling, calendering, stirring or rollmilling and then pressed into a preselected shape. Next, the push composition is placed in contact with the drug composition. The drug composition, push composition can be placed in contacting arrangement by using a conventional two-layered press. The contacting drug composition and push composition are coated with a semipermeable wall. The wall can be applied by compression coating, molding, spraying, dipping, or air suspension procedures. The air suspension and the air tumbling procedures comprise suspending and tumbling the pressed drug composition and the push composition in a current of air containing the wall forming composition. The dosage forms provided by the invention can embrace many shapes for administering a drug. The dosage form, for example, can be round-shaped, square-shaped, oval-shaped, bean-shaped, or caplet-shaped. The dosage form can be manufactured for sublingual administration, buccal administration or gastrointestinal administration.

In another manufacture, dosage form 10 is manufactured by the wet granulation technique. In the wet granulation technique, the drug and the ingredients comprising the drug composition are blended using an organic cosolvent, such as isopropyl alcohol-methylene dichloride 80/20 v/v (volume/volume) as the granulation fluid. The ingredients forming the drug composition are passed through a 40 mesh screen and thoroughly blended in a mixer. Other optional ingredients comprising the drug composition are dissolved in a portion of the granulation fluid and added to the drug blend with continual mixing in the blender. The granulating fluid is added until a blend is produced, which wet blend is then forced through a 20 mesh screen onto oven trays. The blend is dried for 18 to 24 hours at 50° C. in a forced air oven. The dried granules are then sized through a 20 mesh screen. Next, a lubricant such as magnesium stearate, which has been passed through an 80 mesh screen, is added to the drug screened granules and blended in a V-blender for 5 to 10 minutes. The composition is pressed into a layer, for example, in a 3-station Manesty ® layer press. The speed of the press is set at 30 rpm and the maximum load set at 2 tons. The drug layer is pressed against the push composition and the bi-layer, drug-push core fed to a coating machine.

Another manufacturing process that can be used for providing the drug composition, push composition comprises blending the powdered ingredients comprising the drug composition, or the push composition separately in a fluid bed granulator. After the powdered ingredients are dry blended in the granulator, a granulating fluid, for example, poly(vinylpyrrolidone) in water, is sprayed onto the powders. The coated powders then are dried in the granulator. This process granulates all the ingredients present therein while adding the granulating fluid. After the granules are dried, a lubricant, such as stearic acid or magnesium stearate, is added to the granules in a V-blender and blended 5 to 10 minutes. The granules then are pressed in the manner described above.

DESCRIPTION OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

An osmotic dosage form for the controlled and continuous release of the drug nifedipine, and antianginal drug belonging to the pharmacological drugs called the calcium channel blockers, that inhibits the transmembrane influx of calcium ions into cardiac muscles and smooth muscles is made as follows: first, 200 g of nifedipine, 300 g of hydroxypropylcellulose, possessing a 60,000 molecular weight, 295 g of sodium carboxymethylcellulose, possessing a 90,000 molecular weight and 100 g of polyvinylpyrrolidone possessing a 40,000 molecular weight are blended into a mass and then screened through a 40-mesh screen. Then, the screened composition is placed into a Glatt fluid bed granulator, blended and slightly warmed to 35° C. to yield a homogeneous mass. Next, a granulating solution consisting of 100 g of polyvinylpyrrolidone possessing a 40,000 molecular weight in 400 ml of purified water is sprayed onto the fluidized powders.

After initiation of the spraying cycle, the process is monitored to insure formation of acceptable uniformity. The granules are dried in situ and delumped by screening through a 16-mesh screen. Next, 5 g of magnesium stearate is screened through an 80 mesh screen, added to the granules in the blender, and blended to a uniform composition. The composition produced by this process comprised 20 wt % nifedipine, 30 wt % hydroxypropylcellulose, 29.5 wt % of sodium carboxymethylcellulose, 20 wt % of polyvinylpyrrolidone and 0.5 wt % of magnesium stearate. The composition is divided into a drug formulation for making dosage forms wherein the drug formulation comprises 60 mg of nifedipine, 90 mg of hydroxypropylcellulose, 88.5 mg of sodium carboxymethylcellulose, 60 mg of polyvinylpyrrolidone and 1.5 mg of magnesium stearate.

Next, a push formulation is made in an identical manner. First, 788 g of sodium carboxymethylcellulose comprising a 700,000 molecular weight, 10 g of ferric oxide, and 50 g of polyvinylpyrrolidone comprising a 40,000 molecular weight, are screened through a 40-mesh screen, followed by screening 100 g of sodium chloride through a 60 mesh screen. The two screened materials are blended and warmed to 30° C. in a fluid bed granulator. Next, a granulating solution comprising 50 g of polyvinylpyrrolidone comprising a 40,000 molecular weight in 400 ml of distilled water, is sprayed onto the granules. Next, the granules are blended and added to a fluid bed granulator. A granulating solution of 50 g polyvinylpyrrolidone of 40,000 molecular weight in distilled water is coated onto the granules as prepared in the fluidized bed. Then, the granules are dried in situ and delumped by screening through a 16-mesh screen. Then, two grams of magnesium stearate are screened through an 80 mesh screen, and added to the granules in a blender and blended at moderate blending speed for 7 minutes. The composition formed by this process comprises 78.8 wt % sodium carboxymethylcellulose comprising a 700,000 molecular weight, 10 wt % of sodium chloride, 10 wt % of polyvinylpyrrolidone comprising a 40,000 molecular weight, 1.0 wt % ferric oxide, and 0.2 wt % of magnesium stearate. The same composition, divided into a push composition for forming the second composition in a dosage form comprises, expressed in mg as follows: 118.2 mg sodium carboxymethylcellulose comprising a 700,000 molecular weight, 15 mg of sodium chloride, 15 mg of polyvinylpyrrolidone having a 40,000 molecular weight, 1.5 mg of ferric oxide, and 0.3 mg of magnesium stearate.

The drug composition and the push composition, next are fed to a bilayer tablet press and pressed into a bilayer core. Then, a wall forming composition comprising 90 wt % cellulose acetate comprising a 39.8% acetyl content, and 10 wt % polyethylene glycol comprising a 3350 molecular weight, are dissolved in a 90 wt % methylene chloride and 10 wt % methanol cosolvent and is coated around the bilayer cores in a suspension coater. Then, a 25 mil, 0.650 mm, orifice is laser drilled in the center of the wall facing the drug side.

Next, the delivery devices are dried in a humidity oven to remove any residual solvent. The devices are overcoated with an inert coat to enhance their appearance.

Figure 3:
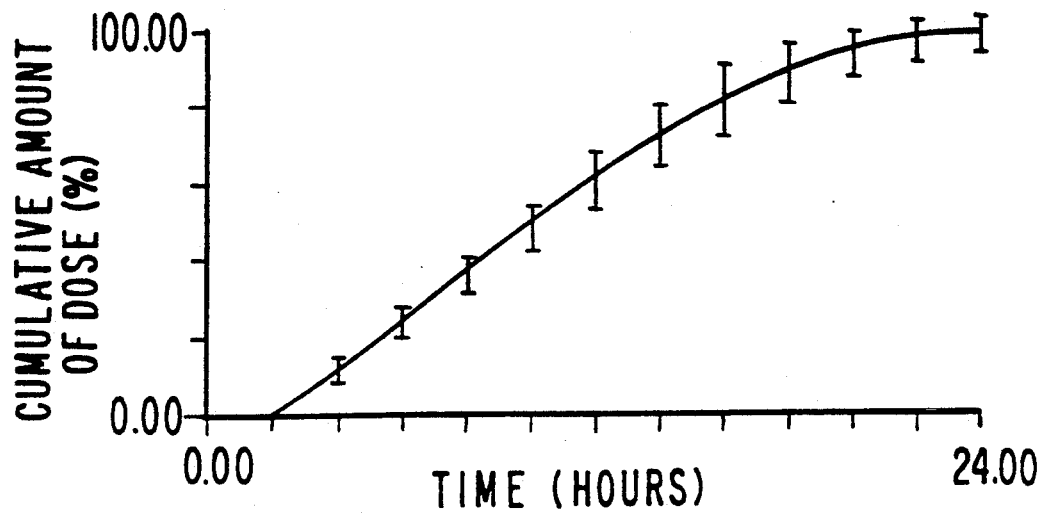
FIG. 3 is a graph that depicts the cumulative amount of drug delivered by the dosage form over time.

The delivery system provided by the present invention uses a carboxymethylcellulose in the drug formulation; and a different and higher molecular weight carboxymethylcellulose in the push formulation. The use of two different molecular weight carboxymethylcellulose polymers provides an unexpected result over the prior art. That is, in the prior art U.S. Pat. No. 4,783,337, a composition prepared according to the patent, comprising a drug and a 200,000 molecular weight polymer, resulted in a residual drug concentration in the dosage form in excess of 11.1%; also a dosage form provided by the prior art comprising a drug and a 300,000 molecular weight polymer leaves a residual concentration of 14.7% drug in the dosage form. The present invention unexpectedly found that a dosage form comprising two different molecular weight carboxymethylcellulose with the higher molecular weight carboxymethylcellulose in the push formulation exhibited as little as 3.7% residual drug in the dosage form at the end of the drug delivery period. This invention's improvement in drug delivery is unforseen and it enhances significantly the use of the present dosage form for improved drug therapy. With the present dosage form, both the physician and the patient know the patient is receiving substantially the intended prescribed dose of drug for drug therapy. The accompanying drawing FIG. 3 denotes the total concentration of a drug, exemplified by nifedipine, delivered over time.

EXAMPLE 2

A formulation for administering a drug to a patient according to claim 1, wherein the formulation comprises a dose amount of an orally administrable drug, a hydroxypropylcellulose, a polyvinylpyrrolidone and a carboxymethylcellulose of 10,000 to 300,000 molecular weight.

EXAMPLE 3

A formulation for administering a drug to a patient according to claim 1, wherein the formulating comprises a dose amount of nifedipine, hydroxypropylcellulose, polyvinylpyrrolidone and carboxymethylcellulose, comprising a 10,000 to 300,000 molecular weight.

EXAMPLE 4

A dosage form for orally administering a drug to a patient is provided according to claim 1, wherein the drug nifedipine is replaced by a member selected from the group consisting of verapamil, diltiazem, bepridil, nicardipine, nitredipine, isradipine, niludepine, nisoldipine, felodipine, cinnarizine, flunarizine, perhexiline, and amlodipine, and wherein the patient is in need of a calcium channel blocking therapy.

EXAMPLE 5

A dosage form for delivering diltiazem is made as follows: first 9.40 kg of diltiazem hydrochloride, 0.20 kg of sodium carboxymethylcellulose comprising a 200,000 molecular weight, 0.10 kg of hydroxypropylcellulose comprising a 30,000 molecular weight are added to a blender and blended for 15 minutes to produce a uniform blend. Next, 0.20 kg of polyvinylpyrrolidone having a 38,000 molecular weight is mixed with 350 ml of anhydrous ethyl alcohol to form a granulation fluid. Then, the granulation fluid is added slowly to the blended ingredients, and all the ingredients blended to produce a wet mass. The wet mass is dried in a forced air oven for 17 to 23 hours at room temperature, about 25° C., to evaporate the ethyl alcohol. Then, the dry granules are given an additional drying for 2 to 4 hours at 50° C. The dry granules are then passed through a 30 mesh screen. Next, 0.10 kg of the lubricant magnesium stearate is added to the drug blend and blended for 9 minutes to produce a homogeneous composition.

Next, a push composition is made as follows: first, 4.35 kg of sodium carboxymethylcellulose having a 650,000 molecular weight, 0.35 kg of sodium chloride and 0.25 kg of hydroxypropylmethylcellulose having a 11,200 molecular weight are blended for 10 minutes to yield a uniform blend. Next, 350 ml of denatured anhydrous ethyl alcohol is added as a granulating fluid to yield a wet mass. Next, the granulated wet mass is passed through a 30 mesh screen to form wet granules. The wet granules next are spread onto trays, and the wet granules dried at room temperature of 25° C. for 20 to 25 hours. The dry granules then are passed through a 20 mesh screen. The push composition now is ready for manufacturing into the final device.

The granules comprising the diltiazem are transferred to the number one feed inlet of a hopper and the granules comprising the push composition are fed to the number two feed inlet of a hopper. The feed hoppers are placed onto a bi-layer press and the diltiazem composition pressed onto the push composition.

Next, the pressed compositions are surrounded with a semipermeable wall. The wall forming composition is prepared as follows: first, a cosolvent is prepared by mixing 80 parts of methylene chloride with 20 parts of methanol (wt/wt) and cellulose acetate having an acetyl content of 39.8% is slowly added thereto. Then, polyethylene glycol having a 3350 molecular weight is added to the freshly prepared ingredients. Then, the pressed dual compositions are placed in a coating unit, and the pressed dual compositions coated with a semipermeable wall.

Next, the wall coated compositions are removed from the coater and an exit port of 24 mil, 0.609 mm, is drilled through the wall by a laser. The dosage forms are dried in a humidity oven at 50% relative humidity at 50° C. for 48 hours to remove wall traces of residual solvent. The dosage forms are sized and shaped for oral admittance into the gastrointestinal tract of a human. The controlled release dosage forms provided by this manufacture comprises a dose of 360 mg of diltiazem that is delivered for a prolonged period of up to 24 hours.

EXAMPLE 6

The above procedures are followed in this example to provide (a) sustained-release, oral osmotic caplets comprising 40 mg, 80 mg, 120 mg, 240 mg or 480 mg of verapamil pharmaceutically acceptable salt; (b) sustained-release, oral osmotic caplets comprising 30 mg, 60 mg, 90 mg, 120 mg, 240 mg or 480 mg of diltiazem pharmaceutically acceptable salt; or (c) extended-release, oral osmotic caplets comprising 20 mg, 30 mg, 45 mg, 60 mg, 90 mg or 120 mg of nifedipine for the relaxation and prevention of coronary artery spasm, for reduction of oxygen requirement and for the reduction of arterial blood pressure.

EXAMPLE 7

The above procedures are followed in this example to provide a dosage form wherein the drug composition comprises the drug nitredipine, polyvinylpyrrolidone, sodium carboxymethylcellulose, comprising a 70,000 molecular weight, sodium lauryl sulphate and hydroxypropylcellulose.

EXAMPLE 8

The above procedure is followed in this example, with the added embodiment comprising blending from 0.1 wt % to 15 wt % of vitamin B₂, also known as riboflavin, with the drug nifedipine for imparting protection against the adverse effects of light on nifedipine, and also blending a surface active agent with the nifedipine to enhance the fluidic dispensing properties of the drug formulation from the dosage form. The surface active agent, operable for the intended purpose, consists of a member selected from the group consisting of anionic, cationic, and nonionic surface active agents, exemplified by Pluronics, Cremophors, polyoxyalkylene fatty acid esters, polyoxyalkylene fatty acid ethers, and alkoxylated hydrogenated castor oils. The surface active agent is present in a concentration of from 0.01 wt % to 15 wt % with the concentration of all ingredients in the formulation equal to 100 wt %.

METHOD OF PRACTICING THE INVENTION

This example pertains to a method for delivering a drug to a human patient in need of therapy, which method comprises:
(A) admitting orally into the human a dosage form comprising:
 (1) a wall comprising at least in part a semipermeable composition, said wall surrounding, defining and forming a compartment, which compartment comprises:
  (a) a drug composition comprising from 10 ng to 750 mg of drug, 20 to 98 wt % of a carboxymethylcellulose comprising a 10,000 to 300,000 molecular weight, 0 to 40 wt % of a hydroxypropylcellulose comprising a 15,000 to 75,000 molecular weight, 0 to 40 wt % of a polyvinylpyrrolidone comprising a 20,000 to 40,000 molecular weight, and 0 to 5 wt % of a lubricant;
  (b) a push composition comprising from 65 wt % to 100 wt % of a carboxymethylcellulose comprising a molecular weight greater than 300,000 to 1,200,000, and from 0 to 25 wt % of an osmagent, and from 0 to 25 wt % of a polyvinylpyrrolidone comprising a 20,000 to 40,000 molecular weight;
 (2) a passageway in the wall for delivering the drug from the device; and,
(B) delivering the drug from the dosage form by imbibing fluid from the patient into the compartment to form a dispensable drug composition and to form an expanding push composition for pushing the drug through the passageway to the human in need of drug therapy.

In summary, it will be appreciated the present invention contributes to the drug delivery art an unobvious dosage form that possesses practical medical utility. While the invention has been described and pointed out in detail with reference to operative embodiments thereof, it will be understood that those skilled in the art will appreciate that various changes, modifications, substitutions and omissions can be made without departing from the spirit of the invention. It is intended, therefore, that the invention embraces those equivalents within the scope of the claims.

We claim:

1. A dosage form for the administration of a drug to a patient, the dosage form comprising:
   (a) a first composition comprising 10 ng to 750 mg of drug;
   (b) a second composition for pushing the first composition from the dosage form;
   (c) a wall surrounding the first and second compositions, said wall comprising at least in part a composition permeable to the passage of fluid; and,
   (d) at least one exit means in the wall for delivering the drug from the dosage form to the patient; and wherein said,
   (e) first composition comprises a carboxymethylcellulose comprising a 10,000 to 300,000 molecular weight; and said,
   (f) second composition comprising a carboxymethylcellulose comprising a molecular weight greater than 300,000 to 1,200,000; and wherein said
   (g) first and second compositions, when the dosage form is in operation, cooperate to deliver substantially all the drug in the dosage form to the patient over time.

2. The dosage form for administering the drug to the patient according to claim 1, wherein the carboxymethylcellulose in the first composition is sodium carboxymethylcellulose.

3. The dosage form for administering the drug to the patient according to claim 1, wherein the carboxymethylcellulose in the second composition is sodium carboxymethylcellulose.

4. The dosage form for administering the drug to the patient according to claim 1, wherein the drug is a calcium channel blocker.

5. The dosage form for administering the drug to the patient according to claim 1, wherein the drug is a member selected from the group consisting of nifedipine, verapamil, diltiazem, bepridil, nicardipine, nitredipine, isradipine, and niludepine.

6. The dosage form for administering the drug to the patient according to claim 1, wherein the drug is a member selected from the group consisting of nisoldipine, felodipine, cinnarizine, flunarizine, perhexiline and amlodipine.

7. The dosage form for administering the drug to the patient according to claim 1, wherein the drug in the first composition is nifedipine and the composition additionally comprises hydroxypropylcellulose.

8. The dosage form for administering the drug to the patient according to claim 1, wherein the drug in the first composition is nifedipine, and the composition additionally comprises polyvinylpyrrolidone.

9. A first composition comprising 10 ng to 750 mg of a drug and a carboxymethylcellulose comprising a 10,000 to 300,000 molecular weight; a second composition comprising a carboxymethylcellulose comprising a molecular weight greater than 300,000 to 1,200,000; and wherein said first composition and second composition are in bilayer arrangement.

10. A dosage form for administering drug to a patient in need of therapy wherein, the dosage form comprises:
   (a) a first composition comprising 10 ng to 750 mg of a drug, riboflavin, a surface active agent and a carboxymethylcellulose comprising a 10,000 to 300,000 molecular weight;
   (b) a second composition for pushing the first composition from the dosage form comprising a carboxymethylcellulose comprising a molecular weight greater than 300,000 to 1,200,000; and, (c) at least one exit means in the wall for delivering the drug from the dosage form to the patient.

11. The dosage form for administering the drug to the patient according to claim 10, wherein the drug is a member selected from the group consisting of nifedipine, verapamil, diltiazem, bepridil, nicardipine, nitredipine, isradipine and niludepine.

12. The dosage form for administering the drug to the patient according to claim 10, wherein the drug is a member selected from the group consisting of nisoldipine, felodipine, cinnarizine, flunarizine, perhexiline and amlodipine.

13. A first composition comprising 10 ng to 750 mg of a drug, riboflavin, a surface active agent and a carboxymethylcellulose comprising a 10,000 to 300,000 molecular weight; a second composition comprising a carboxymethylcellulose comprising a molecular weight greater than 300,000 to 1,200,000; and wherein said first composition and second composition are in bilayer arrangement.

* * * * *